US006663873B2

(12) United States Patent
Doidge et al.

(10) Patent No.: US 6,663,873 B2
(45) Date of Patent: *Dec. 16, 2003

(54) ANTIGENIC PREPARATION FOR TREATMENT OR PREVENTION OF HELICOBACTER INFECTION

(75) Inventors: Christopher Vincent Doidge, Box Hill (AU); Adrian Lee, Lane Cove (AU); Fiona Jane Buck, Malabar (AU); Elizabeth Pietrzykowski, Essendon (AU); Charles Alexander Quinn, Pascoe Vale (AU); Ian George Barr, Templestowe (AU); Michael John Kleinig, Brunswick (AU)

(73) Assignee: CSL, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 08/687,434

(22) PCT Filed: Feb. 17, 1995

(86) PCT No.: PCT/AU95/00077

§ 371 (c)(1),
(2), (4) Date: Aug. 9, 1996

(87) PCT Pub. No.: WO95/22563

PCT Pub. Date: Aug. 24, 1995

(65) Prior Publication Data

US 2002/0122794 A1 Sep. 5, 2002

(30) Foreign Application Priority Data

Feb. 17, 1995 (AU) .............................................. PM 3995

(51) Int. Cl.[7] ........................ A61K 39/00; A61K 39/02; A61K 45/00; A61K 39/385
(52) U.S. Cl. ................................ 424/234.1; 424/184.1; 424/150.1; 424/434; 424/193.1; 424/278.1; 424/197.1; 424/283.1; 424/130.1; 424/137.1; 424/141.1; 424/93.4; 514/54; 514/2; 514/12
(58) Field of Search ............................ 424/150.1, 93.4, 424/184.1, 434, 193.1, 197.11, 234.1, 278.1, 283.1, 130.1, 137.1, 141.1; 514/54, 2, 12

(56) References Cited

U.S. PATENT DOCUMENTS

| 5,403,718 | A | * | 4/1995 | Dorward et al. |
| 5,580,563 | A | * | 12/1996 | Tam |
| 5,712,102 | A | * | 1/1998 | Darveau et al. |
| 5,843,460 | A | * | 12/1998 | Labigne et al. |
| 5,858,352 | A | * | 1/1999 | Pace et al. |
| 5,869,066 | A | * | 2/1999 | Pace et al. |
| 5,871,749 | A | * | 2/1999 | Doidge et al. |
| 5,897,475 | A | * | 4/1999 | Pace et al. |
| 5,997,881 | A | * | 12/1999 | Powell et al. |
| 6,005,090 | A | * | 12/1999 | Doidge et al. |
| 6,129,923 | A | * | 10/2000 | Doidge et al. |
| 6,395,879 | B1 | * | 5/2002 | Mandrell et al. |
| 6,406,703 | B1 | * | 6/2002 | Doidge et al. ............ 424/234.1 |
| 6,468,545 | B1 | * | 10/2002 | Doidge et al. ............ 424/234.1 |
| 6,576,244 | B1 | * | 6/2003 | Weltzin et al. ............ 424/234.1 |
| 2002/0122794 | A1 | * | 9/2002 | Doidge ..................... 424/130.1 |
| 2002/0146423 | A1 | * | 10/2002 | Doidge et al. ............ 424/184.1 |

FOREIGN PATENT DOCUMENTS

| AU | 90/67676 | 12/1993 |
| WO | 93/20843 | 10/1993 |

OTHER PUBLICATIONS

Campbell, Lab. Techniques in Biochemistry & Molecular Biology. vol. 23 pp 1–49, 1991.*
Aspivall et al, Biochemistry 35: 2489–97, 1996.*
Monteiro et al, JBC, 273/19: 11533–543, 1998.*
Drouet et al Infection & Immunity 61/6: 2732–36, 1993.*
Amano, Akita J. Med. 24: 101–108 w/English Translation, 1997.*
Piotrowski et al, Gen. Pharmac. 25/5: 969–976, 1994.*
Moran FEMS Immunology & Medical Microbiology 10: 271–280, 1995.*
Mai et al Gastroenterology 98(5 Pt. 2) p A662, 1990.*
Mills et al, SOMED, 4(S) Abstract# H8–1 p. 5171, Oct. 1991.*
Fumarola et al Clinical Infectious Dis. 14: 365, 1992.*
Mai et al, J. Clinical Investigation 87: 894–900, Mar. 1991.*
Young et al, Gastroenterology 102/4 part 2: p. A716, 1992.*
Conrad et al Current Microbiology 24: 165–169, 1992.*
Lee et al In: Helicobacter pylori: basic mechanisms to clinical cure. Ed. Hunt et al. Kluwer Academic pp 169–179, 1994.*
McGee et al, Curr. Opin. Gastroenterol. 16: 24–31, 2000.*
Pece et al; Recenti Progressi in Medicina 56/5: 237–241, 1997.*
Birkholz et al. (1993) FEMS Immunology and Medical Microbiology. vol. 6, 317–324.*
Nielsen, H., et al., "Neutrophil Activation by Helicobacter Pylori Lipopolysaccharides", The Journal of Infectious Diseases, pp. 135–139, vol. 170, No. 1 (1994).
Piotrowski, J. et al., "Inhibition of Gastric Mucosal Laminin Receptor buy Helicobacter Pylori Lipopolysaccharide: Effect of Ebrotidine", Biochemistry International, pp. 131–138, vol. 27, No. 1 (1992).
Slomiany, B.L. et al., "Inhibition of Gastric Mucosal Laminin Receptor by Helicobacter Pylori Lipopolysaccharide", Biochemical and Biophysical Research Communications, pp. 963–970, vol. 175, No. 3 (1991).

(List continued on next page.)

Primary Examiner—N. M. Minnifield
(74) Attorney, Agent, or Firm—Foley & Lardner

(57) ABSTRACT

An antigenic preparation for use in the treatment or prevention of Helicobacter infection in a mammalian host, comprises the lipopolysaccharide (LPS) of Helicobacter bacteria, particularly the LPS of *H. pylori* or *H. felis*, or an immunogenic fragment thereof.

14 Claims, No Drawings

OTHER PUBLICATIONS

Liau, Y.H. et al., "Helicobacter Pylori Lipopolysaccharide Effect on the Synthesis and Secretion of Gastric Sulfomucin", Biochemical and Biophysical Research Communications, pp. 1411–1417, vol. 184, No. 3 (1992).

Geis, G. et al., "Unusual Fatty Acid Substitution in Lipids and Lipopolysaccharides of Helicobacter Pylori", Journal of Clinical Microbiology, pp. 930–932, vol. 28, No. 5 (1990).

Mills, S.D. et al., "Antigenicity of Helicobacter Pylori Lipopolysaccharides", Journal of Clinical Microbiology, pp. 3175–3180, vol. 30, No. 12 (1992).

Drouet, E.B. et al., "Partial Characterization of an External Polysaccharide of Helicobacter Pylori by using an Immunoglobulin M Monoclonal Antibody", Infection and Immunity, pp. 2732–2736, vol. 61, No. 6 (1993).

Moran, A.P. et al., "Composition Analysis of Helicobacter Pylori rough–Form Lipopolysaccharides", Journal of Bacteriology, pp. 1370–1377, vol. 174, No. 4 (1992).

Mattsby–Baltzer, I. et al., "Lipid A in Helicobacter Pylori", Infection and Immunity, pp. 4383–4387, vol. 60, No. 10 (1992).

Sverbaum, S. et al., "Biochemical Studies of Helicobacter Mustelae Fatty Acid Composition nd Flageua", Infection and Immunity, pp. 1695–1698, vol. 60, No. 4 (1992).

Muotiala, A. et al., "Low Biological Activity of Helicobacter Pylori Lipopolysaccharide", Infection and Immunity, pp. 1714–1716, vol. 60, No. 4 (1992).

Perez–Perez, G.I. et al., "Conservation and Diversity of Campylobacter Pyloridis Major Antigens", Infection and Immunity, pp. 1256–1263, vol. 55, No. 5 (1987).

Mai Uwe, E.H. et al., "Soluble Surface Proteins From Helicobacter Pylori Activate Monocytes/Macrophages by Lipopolysaccharide—Independent Mechanism", Journal of Clinical Investigation, pp. 894–900, vol. 87, No. 3 (1991).

* cited by examiner

ANTIGENIC PREPARATION FOR TREATMENT OR PREVENTION OF HELICOBACTER INFECTION

FIELD OF THE INVENTION

This invention relates to an antigenic preparation and in particular to the use of this antigenic preparation for the treatment and prevention of gastroduodenal disease associated Helicobacter infection, particularly with *Helicobacter pylori* infection in humans.

BACKGROUND OF THE INVENTION

*Helicobacter pylori* is a bacterium that infects the stomach lining of perhaps half the world's population. Infection with the organism is usually chronic, and results in continuing inflammation of the gastric mucosa. The infection is often asymptomatic. However, in association with other cofactors, a proportion of infected people go on to develop sequelae including peptic ulceration of the stomach or duodenum, gastric adenocarcinomas and lymphomas. Peptic ulcer treatment studies have shown that cure of *H. pylori* infection is associated with a dramatic reduction in the relapse rate of this usually chronic disease. Long term infection with *H. pylori* leads to the development of chronic atrophic gastritis, which has long been recognised as a precursor lesion in the development of gastric cancer. Thus a number of studies have now linked preceding *H. pylori* infection with an increased risk of developing gastric cancer. Therefore the treatment and prevention of *H. pylori* infection has the potential to prevent considerable mortality and morbidity from gastroduodenal disease.

There is no laboratory animal model of *H. pylori* infection suitable for use in screening new therapies and vaccines for *H. pylori* infection. However, a *Helicobacter felis* mouse model of gastric Helicobacter infection has been developed that has proved extremely useful in the screening new antimicrobial therapeutic regimens and vaccination protocols (Lee et al. 1990; Dick-Hegedus and Lee, 1991). *H. felis* is a spiral shaped bacterium that is very closely related to *H. pylori*. This bacterium colonises the stomach of mice in a very similar way to *H. pylori* in the human i.e. the main ecological niche is gastric mucus and colonisation is mainly seen in the antrum of the stomach. In germfree mice, *H. felis* infection induces a gastritis that is very similar to the human *H. pylori* infection with a chronic inflammation of mononuclear cells accompanied by a polymorphonuclear leucocyte infiltration. Infection with either organism results in the induction of a similar raised systemic humoral immune response against *H. pylori* and *H. felis* respectively (Lee et al., 1990).

The *H. felis* mouse model has proved to be very predictive of the efficacy of anti-*H. pylori* agents in humans. Thus, monotherapy with agents with high in vitro activity such as erythromycin show no significant in vivo effect against *H. felis* in mice, just as erythromycin has no anti-*H.pylori* effect in humans, despite its high antimicrobial effects in vitro. In contrast, the triple therapy regimens of a bismuth compound, metronidazole, and tetracycline or amoxycillin lead to a very high eradication rate in *H. felis* infected mice (Dick-Hegedus and Lee, 1991). Such triple therapies are the most successful human anti-*H. pylori* regimens, and at the present time are recommended as the first choice for anti-*H. pylori* therapy. The *H. felis* mouse model has also been used to demonstrate that mice can be orally immunised with Helicobacter antigen preparations of sonicated cells and cholera toxin adjuvant, to both treat active *H. felis* infection and to protect against *H. felis* infection, however the protective antigen or antigens in these preparations was not determined (see International Patent Application No. PCT/AU94/00416; Czinn et al., 1993).

In work leading to the present invention, a protective antigen of Helicobacter organisms has been identified, this antigen being recognised by monoclonal antibodies which are effective in treatment of *H. felis*-infected mice.

SUMMARY OF THE INVENTION

In one aspect, the present invention provides an antigenic preparation for use in the treatment or prevention of Helicobacter infection, which comprises the lipopolysaccharide (LPS) of Helicobacter bacteria, or an immunogenic fragment thereof.

Preferably, the antigenic preparation comprises an at least partially purified LPS preparation.

The term "at least partially purified" as used herein denotes a preparation in which the LPS content is greater, preferably at least 30% and more preferably at least 50% greater, than the LPS content of a whole cell sonicate of Helicobacter bacteria. Preferably, the preparation is one in which the LPS is "substantially pure", that is one in which the LPS content is at least 80%, more preferably at least 90%, of the total Helicobacter antigens in the preparation.

It is to be understood that the present invention extends not only to an antigenic preparation comprising the LPS of Helicobacter bacteria, but also to antigenic preparations comprising immunogenic fragments of this lipopolysaccharide, that is LPS fragments which are capable of eliciting a specific protective immune response in a mammalian host. Such immunogenic fragments may also be recognised by Helicobacter-specific monoclonal antibodies, particularly monoclonal antibodies which have a protective or therapeutic effect in relation to Helicobacter infection.

In another aspect, the present invention provides a vaccine composition for use in the treatment or prevention of Helicobacter infection in a mammalian host, which comprises an immunologically effective amount of an antigenic preparation as broadly described above, optionally in association with an adjuvant, together with one or more pharmaceutically acceptable carriers and/or diluents.

In yet another aspect, the present invention provides a method for the treatment or prevention of Helicobacter infection in a mammalian host, which comprises administration to said host of an immunologically effective amount of an antigenic preparation as broadly described above, optionally in association with an adjuvant.

In a related aspect, this invention provides the use of an immunologically effective amount of an antigenic preparation as broadly described above, optionally in association with an adjuvant, for the treatment or prevention of Helicobacter infection in a mammalian host.

In yet another aspect, the invention provides the use of an antigenic preparation as broadly described above, optionally in association with an adjuvant, in the manufacture of a vaccine composition for the treatment or prevention of Helicobacter infection in a mammalian host.

Preferably, but not essentially, the antigenic preparation of this invention is orally administered to the host, and is administered in association with a mucosal adjuvant. However, the invention also extends to parenteral administration of this antigenic preparation.

The present invention also extends to an antibody, particularly a monoclonal antibody, specific for the antigenic preparation as broadly described above, and in particular specific for the LPS of Helicobacter bacteria, including *H. felis* LPS and *H. pylori* LPS.

In this aspect, the invention further provides a method for the treatment or prevention of Helicobacter infection in a mammalian host, which comprises passive immunisation of said host by administration of an effective amount of an antibody, particularly a monoclonal antibody, specific for the antigenic preparation as broadly described above.

By use of the term "immunologically effective amount" herein in the context of treatment of Helicobacter infection, it is meant that the administration of that amount to an individual infected host, either in a single dose or as part of a series, is effective for treatment of Helicobacter infection. By the use of the term "immunologically effective amount" herein in the context of prevention of Helicobacter infection, it is meant that the administration of that amount to an individual host, either in a single dose or as part of a series, is effective to delay, inhibit or prevent Helicobacter infection. The effective amount varies depending upon the health and physical condition of the individual to be treated, the taxonomic group of individual to be treated, the capacity of the individual's immune system to synthesise antibodies, the degree of protection desired, the formulation of the vaccine, the assessment of the medical situation, and other relevant factors. It is expected that the amount will fall in a relatively broad range that can be determined through routine trials.

Throughout this specification and the claims which follow, unless the context requires otherwise, the word "comprise", or variations such as "comprises" or "comprising", is to be understood to imply the inclusion of a stated integer or group of integers but not the exclusion of any other integer or group of integers.

DETAILED DESCRIPTION OF THE INVENTION

Preferably, the antigenic preparation of this invention comprises a preparation of the LPS of *H. pylori* or *H. felis*. Preferably also, this antigenic preparation is used in a vaccine composition for oral administration which includes a mucosal adjuvant.

In a particularly preferred aspect of this invention, an oral vaccine composition comprising an antigenic preparation of at least partially purified *H. pylori* LPS in association with a mucosal adjuvant is used for the treatment or prevention of *H. pylori* infection in a human host.

The mucosal adjuvant which is optionally, and preferably, administered with the at least partially purified Helicobacter LPS preparation to the infected host is preferably cholera toxin. Mucosal adjuvants other than cholera toxin which may be used in accordance with the present invention include non-toxic derivatives of cholera toxin, such as the B sub-unit (CTB), chemically modified cholera toxin, or related proteins produced by modification of the cholera toxin amino acid sequence. These may be added to, or conjugated with, the Helicobacter LPS preparation. The same techniques can be applied to other molecules with mucosal adjuvant or delivery properties such as *Escherichia coli* heat labile toxin. Other compounds with mucosal adjuvant or delivery activity may be used such as bile; polycations such as DEAE-dextran and polyornithine; detergents such as sodium dodecyl benzene sulphate; lipid-conjugated materials; antibiotics such as streptomycin; vitamin A; and other compounds that alter the structural or functional integrity of mucosal surfaces. Other mucosally active compounds include derivatives of microbial structures such as MDP; acridine and cimetidine.

The Helicobacter LPS preparation may be delivered in accordance with this invention in ISCOMS (immune stimulating complexes), ISCOMS containing CTB, liposomes or encapsulated in compounds such as acrylates or poly(DL-lactide-co-glycodside) to form microspheres of a size suited to adsorption by M cells. Alternatively, micro or nanoparticles may be covalently attached to molecules such as vitamin B12 which have specific gut receptors. The Helicobacter LPS preparation may also be incorporated into oily emulsions and delivered orally. An extensive though not exhaustive list of adjuvants can be found in Cox and Coulter, (1992).

Other adjuvants, as well as conventional pharmaceutically acceptable carriers, excipients, buffers or diluents, may also be included in the prophylactic or therapeutic vaccine composition of this invention. The vaccine composition may, for example, be formulated in enteric coated gelatine capsules including sodium bicarbonate buffers together with the Helicobacter LPS preparation and cholera toxin mucosal adjuvant.

The formulation of prophylactic or therapeutic vaccine compositions is well known to persons skilled in this field. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in *Remington's Pharmaceutical Sciences*, 18th Edition, Mack Publishing Company, Pennsylvania, USA. Except insofar as any conventional media or agent is incompatible with the active ingredient, use thereof in the vaccine compositions of the present invention is contemplated.

The Helicobacter LPS preparation of the present invention may be administered as the sole active immunogen in a vaccine composition. Alternatively, however, the vaccine composition may include other active immunogens, including other Helicobacter antigens, as well as immunologically active antigens against other pathogenic species.

It is especially advantageous to formulate the vaccine compositions of this invention in dosage unit form for ease of administration and uniformity of dosage. Dosage unit form as used herein refers to physically discrete units suited as unitary dosages for the human subjects to be treated; each unit containing a predetermined quantity of active ingredient calculated to produce the desired therapeutic effect in association with the required pharmaceutical carrier and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the particular treatment.

In work leading to the present invention, the *H. felis* model described above was used to examine the immune response in immunised and protected mice by generating hybridoma cell lines from fusions of SP-2 cells and lymphocytes from immune mice. These hybridoma cells were screened for the production of monoclonal antibodies that recognised *H. felis*. A hybridoma cell line secreting IgA antibodies that recognised and agglutinated *H. felis* was selected and used to treat infected mice. A significant proportion of these mice were cured of their infection. Thus the antigen recognised by the monoclonal antibody was identified as a protective antigen.

This protective antigen was then identified by biochemical methods as the lipopolysaccharide (LPS) constituent of the outer membrane of the bacteria. The close relationship between H. felis and H. pylori clearly indicates that, as H. felis LPS has been identified as a protective antigen in the mouse model and as vaccination with H. pylori organisms protects mice against subsequent H. felis infection, then H. pylori LPS will be a protective antigen in the human infection. Accordingly, antibodies raised in a mammalian host against the Helicobacter LPS preparation by active vaccination will have the ability to eradicate or at least suppress an existing infection, or prevent establishment of a new infection, in this host. Furthermore, passive immunisation of a mammalian host with antibodies raised against the Helicobacter LPS preparation will similarly eradicate or at least suppress an existing infection, or prevent a new infection, in the host.

Further features of the present invention are more fully described in the following Example(s). It is to be understood, however, that this detailed description is included solely for the purposes of exemplifying the present invention, and should not be understood in any way as a restriction on the broad description of the invention as set out above.

EXAMPLE 1

Experimental Animals

Female 7–8 weeks-old Balb/c specific pathogen free (SPF) mice were obtained from the Animal Breeding and Holding Unit SPF facility, University of NSW. Mice were maintained on a diet of sterile commercial food pellets. Sterile water was given ad libitum.

Bacteria

H. felis (CS1) was grown on Blood Agar Base No.2 with lysed horse blood (5% v/v), and containing amphotericin B (2.5 mg/L), trimethoprim (5 mg/L), polymyxin (1250 IU L), and vancomycin (10 mg/L). Plates were incubated in a microaerophilic atmosphere at 37° C. for 48 hours.

Preparation of Hf Sonicates

H. felis (CS1) was grown on CSA agar, incubated for 48 hours in a microaerophilic environment, and then harvested from the plate in Phosphate Buffered Saline (PBS). The suspension was then centrifuged and resuspended in PBS twice. The bacterial suspension was sonicated in a Branson 450 Sonifer with the Tapered Micro Tip, at Output control setting of 4, 50% Duty Cycle, at a rate of 1 minute per ml of bacterial suspension. The concentration of protein in the resulting sample was determined by the BIORAD DC Protein Assay. Hf sonicates were stored at −20° C.

Preparation of Hybridomas 5 mice were immunised, over 3 weeks, with sonicate of H. felis (Hf) in combination with cholera toxin (CT). All immunisation solutions were diluted in PBS.

| Day 1 | 1 mg Hf + 10 μg CT (0.2 ml OG) |
|---|---|
| Day 8 | as above |
| Day 14 | as above |
| Day 25 | 1 mg Hf (0.2 ml OG) + 100 μg Hf (0.05 ml IV) |

Hybridoma Selection

Hybridomas secreting antibody to H. felis were produced by fusing splenocytes, Peyer's Patches and mesenteric lymph node cells with SP-2/0-Ag14 cells. Procedures were basically as described by MacGregor et al, (1983). The results from the fusions are summarised in Table 1. From the three fusions a total of 87 hybridoma lines were obtained. Of these lines 24 were EIA positive, and were cloned by limiting dilution on 3T3 Balb/c feeder layer in 96 well plates. After cloning, the lines were reassayed for production of specific antibodies. This screening procedure yielded 6 stable lines which secreted antibody which reacted with H. felis sonicate coated on EIA plates.

Enzyme Immunoassay (EIA) for Anti-H. felis Antibodies

Culture supernatants from wells containing hybridomas were screened for antibodies against H. felis by EIA. Plates (Maxisorp/NUNC, Denmark) were coated with H. felis sonicate at 100 ug/ml (diluted from 6.22 mg/ml), in 0.05 M biocarbonate buffer pH 9.6. After overnight incubation at 4° C. the coated plates were blocked by incubation 1 h with 1 mg/ml casein at room temperature, stabilised, dried and sealed. The diluent used in all assays was Blue Diluent (CSL), a PBS-Tween diluent containing casein. Two sets of plates with hybridoma supernatants were incubated for 30 min at 37° C. washed then similarly incubated, one set of plates with HRP conjugated goat anti-mouse IgG gamma specific (KPL, Maryland, USA) and second set of plates with HRP conjugated goat antimouse IGA (KPL, Maryland, USA). Peroxidase activity was measured by addition of substrate solution containing $H_2O_2$ and tetramethylbenzidine. After 5 min at room temperature, the reaction was stopped by addition of 0.05 nm on an automated EIA reader.

Isotyping of the 6 hybridoma lines was performed using a Misotest kit (CSL; Table 1).

TABLE 1

Summary of Results From Fusion Experiments

| Fusion | No wells seeded | No wells with hybridomas | No cloned hybridomas | No stable lines | Isotypes |
|---|---|---|---|---|---|
| HP2-S[1] | 600 | 68 | 23 | 5 | HP2-S.2F7 IgG2a HP2-S.1E8 IgG2a HP2-S.5E10 IgG1 HP2-S.6B7 IgG2a HP2-S.9F4 IgA |
| HP2-PP[2] | 600 | 19 | 1 | 1 | HP2-PP.2F4 IgA |
| HP2-M[3] | 600 | 0 | — | — | |
| TOTAL | 18000 | 87 | 24 | 6 | |

[1]spleen
[2]Peyer's patches
[3]mesenteric lymph nodes

Testing of Therapeutic Effect of Hybridoma Cell Line

Hybridoma line HP2S 9F4 1B11 secreted an IgA antibody that agglutinated freshly grown H. felis, as observed microscopically, and macroscopically through clumping and settling of a bacterial suspension. IgA acts against bacteria colonising mucosal surfaces through a process described as "immune exclusion". For IgA antibodies recognising the surface of mucosal bacteria, a key property is the ability to agglutinate the organisms, thus interfering with their capacity to colonise the mucosal surface. Therefore, the target of a monoclonal IgA antibody that agglutinates a specific bacterium is likely to be a protective antigen.

Mice were infected with H. felis. After the infection was established, groups of mice were inoculated with hybridoma cell lines HP2S 9F4 1B11, or FV4 2C6 2B3 (an anti-influenza IgA secreting cell line, used as a negative control). Another group of infected animals were left untreated. After 21–24 days mice were sacrificed and their infection status determined.

Infection with *H. felis*

*H. felis* (CS 1–87) was grown on CSA agar, and then harvested from the plate in Brain Heart Infusion (BHI) solution. Estimates of total numbers of spiral organisms in the resulting suspension were made using haemocytometer chambers.

Mice were given 3 doses of live *H. felis* in BHI, as follows:

| Day 1: | $1.34 \times 10^8$ Hf/mouse (0.20 ml OG) |
|---|---|
| Day 3: | $1.76 \times 10^8$ Hf/mouse (0.50 ml OG) |
| Day 5: | $3.90 \times 10^8$ Hf/mouse (0.25 ml OG) |

| Day | Hybridoma HP2S 9F4 1B11 [20] | Hybridoma FV4 2C6 2B3 [20] | Infected Control [10] |
|---|---|---|---|
| 1 | Dose H.f. | Dose H.f. | Dose H.f. |
| 3 | Dose H.f. | Dose H.f. | Dose H.f. |
| 5 | Dose H.f. | Dose H.f. | Dose H.f. |
| 30 | Dose Hybridoma cells | Dose Hybridoma cells | |
| 51–54 | Collect 20 | Collect 20 | Collect 10 |

Administration of Hybridomas

On day 30, the coded hybridoma suspensions were resuspended in PBS to give each a final concentration of $1.0 \times 10^7$ cells/ml. $1.0 \times 10^6$ cells (0.1 ml) of the appropriate suspension was administered to each mouse subcutaneously, high above the shoulders, using a 26 G needle.

Collection of Samples 21 days to 24 days following administration of hybridoma cells, with all mice showing significant tumour growth, the animals were anaesthetised and euthanased. Mice were anaesthetised with a mixture (1:5:10) of ketamine (100 mg/ml)/xylazine (20 mg/ml)/water, each mouse receiving approximately 0.15 ml of the mixture I.P. with a 27 G needle. When the mice showed no response to pedal stimulus, they received 0.1 ml I.P. of a 0.1% solution of PV Carpine to induce salivation, and then were placed on their sides, and saliva collected for 5–10 minutes, using a 50 $\mu$L micropipettor, into eppendorf tubes. The saliva was then stored at −20° C.

Mice were then bled, the blood centrifuged and the serum stored at −20° C. The animals were then killed by cervical dislocation. The gall bladder was removed, pierced with a 23 G needle and bile from all mice in a group was collected, as a pool, in an eppendorf tube, and stored at −20° C.

For the first 5 mice from each group, the spleen was removed, rinsed in PBS, placed in a microfuge tube, and stored in liquid nitrogen. The stomach was removed, opened along the lesser curvature, washed vigorously in saline, and half of the stomach placed in formalin for histology. From the remaining half of the stomach, the antral section was placed in a well of urease reagent in a microtitre plate.

Histology

For histology analysis, stomachs fixed in formalin were processed and embedded in paraffin wax. 5 $\mu$m sections were cut, and stained with may Grunwald-Giemsa. To confirm urease results of infection, stomach sections from 5 mice from each group were examined on high power, and graded for the presence of spiral bacteria.

Urease Assay

Urease reagent consists of a 2% w/v urea solution in 0.01 M sodium phosphate buffer, with 0.05% w/v Phenol red as an indicator, 0.02% w/v sodium azide as a preservative, adjusted to pH 6.5.

Results

Urease Results

| Treatment Group | No. of Mice | Number (%) Urease Positive |
|---|---|---|
| Infected Control | 10 | 10 (100%) |
| FV4 2C6 2B3 | 20 | 20 (100%) |
| HP2S 9F4 1B11 | 19 | 13 (68%) |

There is a significant difference (P 0.02) between the number of urease positive mice in the FV4 2C6 2B3 and HP2S 9F4 1B11 treated groups.

Histology Results

The histological analysis of the sample of stomach sections confirmed the urease results i.e. organisms were seen in all five samples from the infected control (urease positive) and all five samples from the mice inoculated with hybridoma cell line FV4 2C6 2B3 (influenza antibody), no organisms were seen in 2 urease negative samples from hybridoma cell line HP2S 9F4 1B11 and organisms were seen in 3 urease positive samples. All histology slides were analysed with the operator blind as to the status of the mice.

Conclusion

The significant, specific clearance of organisms from the stomachs of infected mice receiving HP2S 9F4 1B11 hybridoma cell line, producing antibodies against *H. felis*, as compared to the mice that received FV4 2C6 2B3 hybridoma cell line, producing antibodies against influenza virus, demonstrates that the antigen to which the antibody secreted by HP2S 9F4 1B11 is directed, is a protective *H. felis* antigen.

EXAMPLE 2

Characterisation of the Antigen Recognised by Monoclonal Antibody HP2S 9F4 1B11.

Bacterial strains *H. felis* (CS1) and *H. pylori* (921023) were grown on CSA agar plates. Bacteria were harvested by scraping plates and resuspended in PBS. Sonicates were prepared as described above. Whole cell sonicates were stored at −20° C. until used.

SDS-PAGE and immunoblotting Novex (San Diego, Calif.) tris glycine pre-cast polyacrylamine gels either 12% homogenous gels or 4–20% gradient gels were used in these studies with samples run under reducing conditions in the presence of sodium dodecyl sulphate (SDS). After electrophoresis the separated bacterial components were transferred to nitrocellulose. Gels were also stained for protein by Coomassie blue or by silver stain using the Rapid-Ag-Stain kit (ICN, Irvine, Calif.). The nitrocellulose was blocked for 1 hr in 1% casein before incubation with antibody and subsequently with a Goat anti-mouse IgG+IgM+IgA conjugated with peroxidase. Blots were developed with 4-chloro-1-naphthol.

In some cases the nitrocellulose strips were treated with sodium periodate prior to reacting them with antibody (Woodward et al., 1985). This method oxidises carbohydrate moieties containing vicinal hydroxyl groups and destroys most carbohydrate epitopes. Control strips were incubated in pH 4.5 buffer without sodium periodate.

Extraction of Lipopolysaccharide (LPS)

Two methods were used to purify LPS, these were essentially as described by Mills et al. (1992). Proteinase K digestion was modified from the Hitchcock and Brown (1983) method and a phenol-water extraction procedure that was modified from the Westphal and Jann (1965) method. Samples of LPS were run on SDS-PAGE and in some cases transferred to nitrocellulose as detailed above.

Results

Whole cell sonicates Western blots of *H. felis* when reacted with monoclonal antibody HP2S 9F4 1B11 showed a dense broad band at an approximate MW of 20–23,000 with a number of minor bands in the 45–90,000 MW range. When strips of *H. felis* were incubated with sodium periodate prior to probing with HP2S 9F4 1B11 all reactivity was removed unlike strips incubated in buffer alone which retained their reactivity with HP2S 9F4 1B11.

Proteinase K digestion and phenol water extraction of *H. felis* sonicate removed practically all protein as demonstrated by Coomassie blue staining of SDS-PAGE gels. What remained as detected by a silver stain were a small number of bands less than 50 KD. When this digested material was transferred to nitrocellulose and reacted with HP2S 9F4 1B11, a number of bands were detected with the major bands at approximately 20 and 25 KD with a number of lower intensity bands between and above these bands. When similar blots were reacted with sodium periodate all HP2S 9F4 1B11 reactivity seen previously against these bands was lost.

Conclusion

The antigenic determinant of *H. felis* that the monoclonal antibody HP2S 9F4 1B11 recognises is LPS.

References

1. Cox, J. and Coulter, A. (1992). Advances in Adjuvant Technology and Application. In Animal Parasite Control Utilising Biotechnology. Edited W. K. Yong, CRC Press.
2. Czinn, S. J., Cai, A. and Nedrud, J. G. (1993). Protection of germ-free mice from infection by *Helicobacter felis* after active oral or passive IgA immunization. *Vaccine*, 11:637–642.
3. Dick-Hegedus, E. and Lee, A. (1991). Use of a mouse model to examine anti-*Helicobacter pylori* agents. *Scand. J. Gastrolenterol*. 26:909–915.
4. Hitchcock, P. J. and Brown, T. M. (1983). Morphological heterogeneity among Salmonella lipopolysaccharides chemotypes silver stained polyacrylamide gels. *J.Bacterol*. 164:269–277.
5. Lee, A., Fox, J. G., Otto, G. and Murphy, J. (1990). A small animal model of human *Helicobacter pylori* active chronic gastritis. *Gastroenterology*. 99:1316–1323.
6. MacGregor, A., Kornitschuk, M., Hurrell, J. G. R., Lehman, N. I., Coulepis, A. G., Locarnini, S. A. and Gust, I. D.(1983), *J. Clin. Microbiol*. 18:1237–1243.
7. Mills, S. D., Kurjanczyk, L. A. and Penner, J. L. (1992). Antigenicity of *Helicobacter pylori* lipopolysaccharides. *J. Clin. Microbiol*. 30:3175–3179.
8. Westphal, O., and Jann, K. (1965). Bacterial lipopolysaccharides: extraction with phenol-water and further applications of the procedure. *Methods Carbohydr. Chem*. 5:83–91.
9. Woodward, M. P., Young, W. W. and Bloodgood R. A. (1985). Detection of monoclonal antibodies specific for carbohydrate epitopes using periodate oxidation. *J.Immunol. Methods* 78:143–153.

What is claimed is:

1. A composition for use in the treatment or prevention of *Helicobacter pylori* or *Helicobacter felis* infection in a mammalian host by eliciting a mucosal immune response in said host, which composition comprises (A) an immunologically effective amount of an antigenic preparation comprising an at least partially purified lipopolysaccharide (LPS) of Helicobacter bacteria or an immunogenic fragment thereof which elicits said mucosal immune response, (B) a compound with adjuvant activity and (C) one or more pharmaceutically acceptable carriers or diluents.

2. A composition according to claim 1, which comprises the LPS of *H. pylori* or *H. felis*, or an immunogenic fragment thereof.

3. A composition according to claim 1, wherein the adjuvant is a mucosal adjuvant.

4. A composition according to claim 1, wherein said antigenic preparation comprises the LPS of *H. pylori* or *H. felis*.

5. A composition according to claim 1, wherein said composition comprises a purified Helicobacter lipopolysaccharide preparation.

6. A method for the treatment or prevention of *Helicobacter pylori* or *Helicobacter felis* infection in a mammalian host by eliciting a mucosal immune response in said host, comprising administering to said host an immunologically effective amount of an antigenic preparation comprising an at least partially purified lipopolysaccharide (LPS) of Helicobacter bacteria, or an immunogenic fragment thereof, to elicit said mucosal immune response.

7. A method according to claim 6, wherein said antigenic preparation comprises the LPS of *H. pylori* or *H. felis*, or an immunogenic fragment thereof.

8. A method according to claim 6, wherein said antigenic preparation is administered in association with an adjuvant.

9. A method according to claim 8, wherein said adjuvant is a mucosal adjuvant.

10. A method according to claim 6, wherein said antigenic preparation is orally administered to said host.

11. A method according to claim 6, wherein said antigenic preparation is parenterally administered to said host.

12. A method according to claim 6, wherein said host is a human.

13. A method according to claim 6, wherein said antigenic preparation comprises a purified Helicobacter lipopolysaccharide preparation.

14. A method according to claim 6, wherein said antigenic preparation comprises the LPS of *H. pylori* or *H. felis*.

* * * * *